(12) United States Patent
Ota et al.

(10) Patent No.: US 8,037,739 B2
(45) Date of Patent: Oct. 18, 2011

(54) METHOD FOR ANALYZING SAMPLE IN LIQUID

(75) Inventors: Masahiro Ota, Kyoto (JP); Noriaki Oyabu, Osaka (JP); Hiroaki Adachi, Osaka (JP); Masayuki Abe, Osaka (JP); Seizo Morita, Osaka (JP); Yusuke Mori, Osaka (JP); Takatomo Sasaki, Osaka (JP)

(73) Assignee: Shimadzu Corporation, Kyoto (JP)

( * ) Notice: Subject to any disclaimer, the term of this patent is extended or adjusted under 35 U.S.C. 154(b) by 161 days.

(21) Appl. No.: 12/197,108

(22) Filed: Aug. 22, 2008

(65) Prior Publication Data
US 2011/0048115 A1    Mar. 3, 2011

(30) Foreign Application Priority Data
Aug. 29, 2007   (JP) .................................. 2007-223212

(51) Int. Cl.
*G01N 11/00* (2006.01)
(52) U.S. Cl. ..................................... 73/53.01
(58) Field of Classification Search .............. 73/53.01, 73/64.53, 64.52, 105; 250/306
See application file for complete search history.

(56) References Cited

U.S. PATENT DOCUMENTS

| | | | | |
|---|---|---|---|---|
| 5,831,153 A | * | 11/1998 | Binnig et al. ................... | 73/105 |
| 5,939,623 A | * | 8/1999 | Muramatsu et al. ............ | 73/105 |
| 7,114,405 B2 | * | 10/2006 | Sunwoldt et al. ............ | 73/866.5 |
| 2004/0026618 A1 | * | 2/2004 | Nakamura ..................... | 250/306 |
| 2010/0267164 A1 | * | 10/2010 | Adams et al. .................. | 436/183 |

FOREIGN PATENT DOCUMENTS

| | | |
|---|---|---|
| CN | 2630837 | 8/2004 |
| JP | 2002-286614 | 10/2002 |

OTHER PUBLICATIONS

Chinese First Examination Report of China Application No. 200810129971.0, dated May 21, 2010.

* cited by examiner

*Primary Examiner* — Hezron E Williams
*Assistant Examiner* — Tamiko Bellamy
(74) *Attorney, Agent, or Firm* — J.C. Patents

(57) ABSTRACT

A method for analyzing a sample in a liquid is provided, which is suitable for easily and reliably preventing a liquid for analysis from being evaporated. When the sample in the liquid is observed by using a scanning probe microscope (SPM), a sealing liquid (17) immiscible with a liquid for analysis (16) is filled around the liquid for analysis (16), in which a sample (13) and a probe (15) are immersed, so as to form a sealing state, in which the liquid for analysis (16) is isolated from an external gas. The SPM enables the probe (15) disposed on a front end of a cantilever (14) to approach a surface of the sample (13) immersed in the liquid, scans the surface of the sample, and detects an interaction between the sample (13) and the probe (15), thereby generating an image.

17 Claims, 3 Drawing Sheets

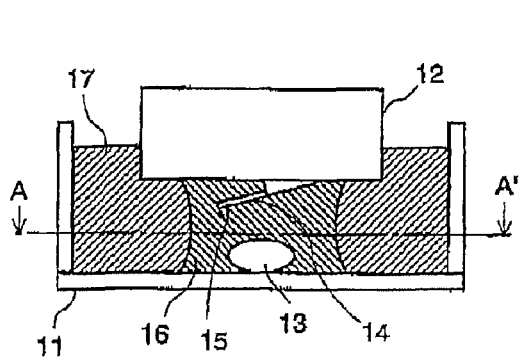
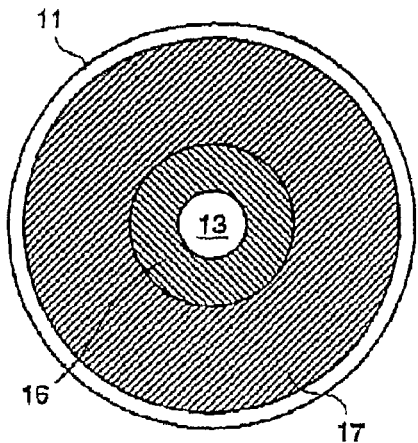
FIG. 1(a)    FIG. 1(b)
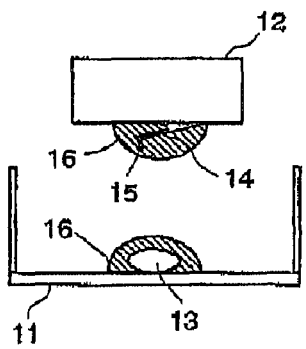
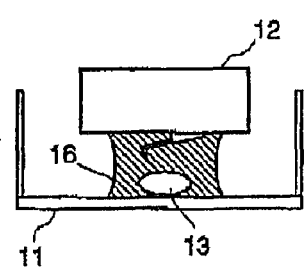
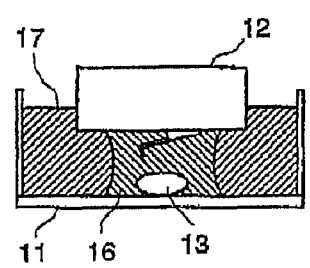
FIG. 2(a)    FIG. 2(b)    FIG. 2(c)
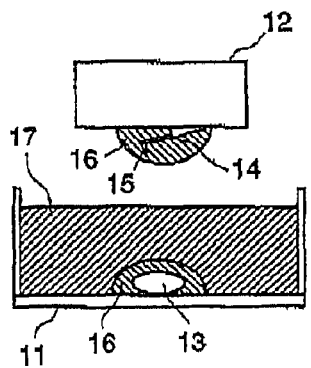
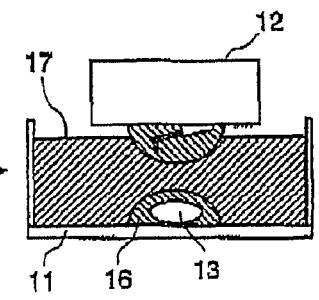
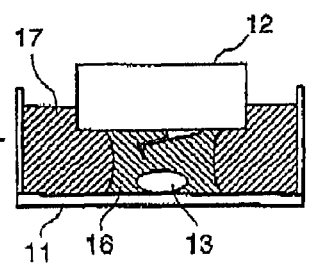
FIG. 3(a)    FIG. 3(b)    FIG. 3(c)

METHOD FOR ANALYZING SAMPLE IN LIQUID

CROSS-REFERENCE TO RELATED APPLICATION

This application claims the priority benefit of Japan application serial no. 2007-223212, filed Aug. 29, 2007. All disclosure of the Japan application is incorporated herein by reference.

BACKGROUND OF THE INVENTION

1. Field of the Invention

The present invention generally relates to a method for analyzing a sample in a liquid through using a scanning probe microscope (SPM) or a cantilever sensor.

2. Description of Related Art

SPM is a type of microscope for scanning a surface of a sample through a tiny probe and meanwhile detecting an interaction between the probe and the sample, so as to detect a shape or physical quantity of the surface of the sample, thereby generating an image. The SPM includes a scanning tunnelling microscope (STM) using a current flowing between the probe and the sample to represent the interaction there-between, or an atomic force microscope (AFM) using an atomic force between the probe and the sample to represent the interaction therebetween.

As described above, the SPM turns the interaction between the probe and the surface of the sample into an image, so as to have the following characteristics. That is, not only a sample disposed in vacuum or in the atmosphere can be observed, a sample disposed in a liquid can also be observed. To observe the sample in a liquid is implemented by using a structure, called a liquid cell, as shown in FIG. 6(a).

A sample 33 is placed in a sample holder 31, which has an opened upper surface and is capable of being fully filled up with a liquid, and a cantilever 34 with a probe 35 on a front end thereof is fixed on a base 32 and is installed on a main body of the microscope. When conducting observations in a liquid, a liquid 36 is fed into the sample holder 31 to a level that both the sample 33 and the probe 35 close to the sample 33 are immersed in the liquid 36. At this time, the liquid 36 in the sample holder 31 contacts with an external gas; as time elapses, the liquid 36 is evaporated, such that the liquid volume is reduced. During the observation, if the temperature of the liquid 36 is changed due to the evaporation, the sample 33 and the probe 35 may be thermally expanded (or shrunk); accordingly, an observation visual field may change, as the time elapses. The phenomenon is called a thermal drift, which is the reason why the distortion of the observed image occurs in SPM.

In addition, the following problems may also occur. As the temperature of the liquid change due to the evaporation of the liquid 36, the state on the surface of the sample changes accordingly, or the substance dissolved in the liquid 36 may be precipitated to contaminate the surfaces of the sample 33, the cantilever 34, and the probe 35. In addition, as for the AFM with a mechanism for detecting upper and lower displacements of the cantilever 34 by using a laser beam, as shown in FIG. 6(b), if a liquid level is lowered due to evaporation and a space is formed in an optical path of the laser, it is necessary to adjust a position of a laser source and a position of an optical detector once again. In view of the above reasons, in order to stably observe the surface of the sample for a long time, it is necessary to restrain the evaporation of the liquid in which the sample is immersed therein (hereafter referred to as "liquid for analysis").

[Patent Document 1] Japanese Laid-Open Patent Publication NO. 2002-286614 (see [0016], FIG. 2)

As one of the solutions for preventing the evaporation of the liquid for analysis, in the conventional art, a known method using a packing to surround the sample and the liquid for analysis, so as to form a sealing space. In the above method, as shown in FIG. 7, the packing 41 formed by an O ring is clamped between the base 32, which secures s the cantilever 34, and the planar sample holder 31, such that the sample 33 and the liquid for analysis 36 are sealed within a sealing space surrounded by the sample holder 31, the base 32, and the packing 41, thereby preventing the evaporation of the liquid for analysis 36. However, when using such a method, the packing 41 is usually in the form of solid, and it is difficult to further deform after the packing 41 is collapsed to a certain extent, so it must enable a distance between the probe 35 and the surface of the sample to approach an observable distance (smaller than or equal to 1 nm) within a collapsing amount d of the packing 41. Therefore, the thickness of the sample 33 must be accurately determined with the consideration of the collapsing amount d. However, during the actual observation, it is quite difficult to accurately determine the thickness of the sample 33 for processing. Furthermore, the relative movement between the base 32 and the sample holder 31 is limited by the packing 41; thus when the observation position changes, the sample 33 or the probe 35 cannot be moved along a horizontal direction and a vertical direction to a large extent. In addition, the packing 41 usually adopts O rings made of rubber; but when an organic solvent is used as the liquid for analysis 36, the packing 41 may be dissolved by the organic solvent.

On the other hand, when it is difficult to seal the liquid for analysis, a relatively large amount of liquid for analysis is used in consideration of the evaporation. Therefore, it is possible to reduce the variation of the entire liquid for analysis with respect to the evaporated amount. However, as for the structure of the SPM, the amount of liquid for analysis that can be fed into the sample holder is limited, and when an organic solvent with a high evaporation speed is used, it is difficult to observe the sample for a long time. In addition, the following situation also exists, that is, some types of liquids for analysis may generate toxic gases during evaporation, so that the above process cannot be performed. Furthermore, if the liquid for analysis is an aqueous solution, the concentration may change due to the evaporation of the moisture.

In addition, in the method for preventing the volatilization of the liquid for analysis disclosed in the Patent Document 1, a liquid layer is disposed on the surface of the liquid used for the analysis for preventing the volatilization, wherein the liquid layer is formed by a liquid immiscible with the liquid for analysis. However, when the liquid layer for preventing the volatilization is formed on the liquid for analysis in this manner, a liquid with a specific weight smaller than that of the liquid for analysis is required to be used for forming the liquid layer. Furthermore, it is necessary to fill the liquid for analysis into the sample holder to such a level that both the sample and the probe are immersed therein, and a liquid level is formed within the sample holder; hence, a large amount of liquid for analysis is required. In addition, if a gas-liquid interface exists in the optical path of the laser for detecting the displacement of the cantilever, the sloshing of the liquid level may interfere with the optical path. Therefore, in the Patent Document 1, a method for eliminating the above problem is described, wherein a laser source and an optical detector are disposed in the liquid, or an optical fiber is disposed in the liquid for guiding the laser beam and capturing the reflected light. However, the above method has a problem that the adjustment of positions of the laser source and the optical detector, or the optical fiber is rather complicated.

SUMMARY OF THE INVENTION

Accordingly, the present invention is directed to a method for analyzing a sample in a liquid, which is suitable for eliminating problems in the conventional art and can easily and reliably prevent the evaporation of a liquid used for the analysis.

As embodied and broadly described herein, a method for analyzing a sample in a liquid is provided in the present invention, in which an SPM is used, and a probe disposed on a front end of a cantilever is made to approach a surface of the sample immersed in the liquid, scans the surface of the sample, then detects an interaction between the sample and the probe, thereby generating an image. The method for analyzing the sample in the liquid is characterized by filling a sealing liquid, immiscible with a liquid for analysis, around the liquid for analysis, wherein the sample and the probe are immersed in the liquid for analysis, so as to form a sealing state, in which the liquid for analysis is isolated from external gas.

For example, the sealing state may be formed through the following steps, including: adhering liquid drops of the liquid for analysis to an inner part of a sample holder, which has an opened upper surface and is capable of being fully filled up with a liquid; adhering the liquid drops of the liquid for analysis to a lower surface of a base having a fixed cantilever in a manner of surrounding the cantilever; making the base to approach the sample holder, so as to blend the liquid drops of the liquid for analysis respectively adhered to the base and the sample holder; and feeding the sealing liquid into the sample holder, so as to fill the sealing liquid around the liquid for analysis.

In addition, the sealing state may also be formed through the following steps, including: adhering the liquid drops of the liquid for analysis to an inner part of a sample holder, which has an opened upper surface and is capable of being fully filled up with a liquid; filling the sealing liquid into the sample holder, so as to fill the sealing liquid around the liquid drops of the liquid for analysis; adhering the liquid drops of the liquid for analysis to a lower surface of a base having a fixed cantilever in a manner of surrounding the cantilever; and making the base approach the sample holder, so as to blend the liquid drops of the liquid for analysis respectively adhered to the base and the sample holder.

Furthermore, in the step of adhering the liquid drops of the liquid for analysis to the inner part of the sample holder, the sample used as an analytical object is disposed in the liquid drops.

In addition, the method for analyzing the sample in a liquid of the present invention may not only be applied to analyze surface properties of a sample by using the SPM, but also applied to detect minor constituents in the liquid by using a cantilever sensor. In the method for analyzing the sample in a liquid of the present invention, the cantilever sensor is used to enable a cantilever, in which a substance is fixed on the surface of the cantilever and the substance is capable of absorbing an object substance, to immerse in the liquid, and detects the object substance by detecting an interaction between the object substance dissolved or dispersed in the liquid and the surface of the cantilever. The method for analyzing the sample in the liquid is characterized by filling a sealing liquid, immiscible with a liquid for analysis around the liquid for analysis in which the cantilever is immersed therein, so as to form a sealing state, in which the liquid for analysis is isolated from external gas.

Furthermore, in the method for analyzing the sample in the liquid of the present invention, the base or the sample holder for fixing the cantilever preferably has a liquid injection mechanism, which is used for injecting a liquid into the liquid for analysis after the sealing state is formed. Through using the base or the sample holder, for example, during the process of analyzing the sample in the liquid by using the cantilever sensor, once the sealing state is formed, the liquid injection mechanism is used to feed the sample liquid into the liquid for analysis, so as to easily detect the changes of the behaviour of the cantilever before and after the sample liquid is fed into the liquid for analysis.

Furthermore, in the present invention, the so-called "liquid for analysis" refers to a liquid used for immersing the sample and the probe when the SPM is used for an observation (that is, when the surface properties are analyzed); or refers to a liquid used for immersing the cantilever when the cantilever sensor is used for an analysis. Besides pure water or aqueous solution, the liquid for analysis may also be any other type of liquid, such as oil, organic solvent, and the like, which is appropriately selected corresponding to the type of the sample or the analysis object. In addition, the sealing liquid may be any type of liquid, as long as it is immiscible with the liquid for analysis. When pure water or aqueous solution is used as the liquid for analysis, oil, for example, may be used as the sealing liquid. For example, if Fluor-inert liquids, which is immiscible with water, and organic solvent are used as the sealing liquid, such sealing liquid can cope with various liquids for analysis.

EFFECTS OF THE INVENTION

In the method for analyzing the sample in the liquid according to the present invention, the sealing liquid is used to surround and seal the liquid for analysis, so as to reliably prevent the evaporation of the liquid for analysis; accordingly, the sample in the liquid can be analyzed with a high accuracy. In addition, the O ring and other solid packing are not used, so that it is not necessary to strictly control the thickness of the sample; accordingly, the moving scope of the probe is not limited to a large extent. Furthermore, the sealing liquid may be any type of liquid, as long as it is immiscible with the liquid for analysis, and is not limited to a liquid with a specific weight smaller than that of the liquid for analysis as used in the conventional art. In addition, the sealing liquid is used to surround the liquid for analysis; hence, it is advantageous that a relatively small amount of the liquid for analysis is used. It is especially preferable when various liquids are being used and adjusted, which would be time-consuming, or when expensive liquids are used as the liquid for analysis. Furthermore, in addition to the above effects, in the method for analyzing the sample in the liquid of the present invention, when the displacement of the cantilever is detected by using a laser, the optical path of the laser is not being interfered by the sloshing of the liquid level because there is no gas-liquid interface existed in the optical path of the laser.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

FIGS. 1(*a*) and 1(*b*) are cross-sectional views of a structure of a liquid cell when a liquid used for the analysis is in a sealing state according to a method for analyzing a sample of the present invention.

FIGS. 2(*a*), 2(*b*), and 2(*c*) are views of a sequence for forming the sealing state according to an embodiment of the present invention.

FIGS. 3(*a*), 3(*b*), and 3(*c*) are views of a sequence for forming the sealing state according to another embodiment of the present invention.

DESCRIPTION OF THE EMBODIMENTS

Figure 4:
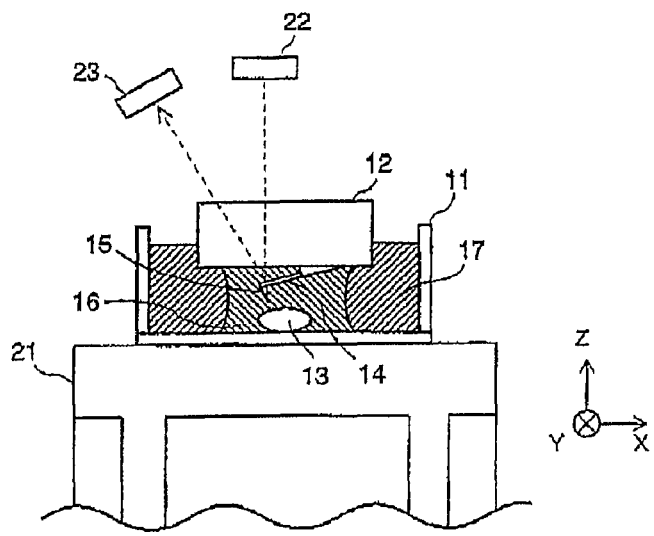
FIG. 4 is a schematic view of a main structure when an AFM is used to observe the sample in the solution cell.

Reference will now be made in detail to the present embodiments of the invention, examples of which are illustrated in the accompanying drawings. Wherever possible, the same reference numbers are used in the drawings and the description so as to refer to the same or like parts.

The best aspect for implementing the present invention is described below with reference to the accompanying drawings. FIG. 1 is a view of a structure of a liquid cell used in a method for analyzing a sample according to the present invention, in which FIG. 1(*a*) is a side cross-sectional view, and FIG. 1(*b*) is an cross-sectional view taken along a line of arrow A-A' in FIG. 1(*a*). A sample holder 11 is configured as having an opened upper surface, and the interior of the sample holder is capable of being fully filled up with a liquid. A cantilever 14 is fixed on a lower surface of a base 12 formed by a transparent material, such as glass, and a tiny probe 15 is disposed on a front end of the cantilever 14. In the drawing, the numeral 13 depicts a sample, the numeral 16 depicts a liquid used for the analysis, and the numeral 17 depicts a sealing liquid. The sample 13, the probe 15, and the cantilever 14 are immersed in the liquid for analysis 16. The liquid for analysis 16 is surrounded by the sealing liquid 17, so that a sealing state is formed and the liquid for analysis 16 is isolated from external gas due to the sealing liquid 17. Here, an appropriate type of liquid corresponding to the sample 13 is used as the liquid for analysis 16. The sealing liquid 17 may be any type of liquid, so long as it is immiscible with the liquid for analysis 16. For example, when pure water or aqueous solution is used as the liquid for analysis 16, oil is used as the sealing liquid 17. In addition, if a Fluor-inert liquid immiscible with water and organic solvents is used as the sealing liquid 17, it copies compatible with various liquids for analysis 16.

FIG. 2 shows a sequence for forming a sealing state. First, a liquid drop of the liquid for analysis 16 is adhered to the centre of a bottom surface of the sample holder 11, and the sample 13 is disposed in the liquid drop. Next, a liquid drop of the liquid for analysis 16 is also adhered to a lower surface of the base 12 (shown in FIG. 2(*a*)) in a manner of covering the probe 15 and the cantilever 14. Then, the base 12 is made to approach the sample holder 11 from an upper side thereof, such that the liquid drop on the lower surface of the base 12 is blended with the liquid drop in the sample holder 11 (shown in FIG. 2(*b*)). At this time, under surface tension, the liquid for analysis 16 is maintained between the base 12 and the sample holder 11, which are opposite to each other, and the liquid for analysis 16 forms an approximate cylindrical shape. Then, the sealing liquid 17 is slowly fed into the sample holder 11, so that the sealing liquid 17 is filled around the liquid for analysis 16. In this manner, peripheral sides (the surfaces except the part contacting with the sample holder 11 and the base 12) of the liquid for analysis 16, which is cylindrical shape, are surrounded by the sealing liquid 17, such that the liquid for analysis 16 is isolated from the external gas (shown in FIG. 2(*c*)).

In addition, the sealing state may be alternatively formed according to a sequence shown in FIG. 3. In such a sequence, before the probe 15 and the cantilever 14 are made to approach the sample 13, the sealing liquid 17 is used to surround the liquid for analysis 16. Since this manner can prevent the evaporation of the liquid for analysis 16 under a state that only the sample 13 exists, it is applicable for the circumstance that the sample 13 needs to be delivered after being placed in the sample holder 11. First, same as the above sequence, a liquid drop of the liquid for analysis 16 is formed on the centre of a bottom surface of the sample holder 11, and the sample 13 is disposed in the liquid drop. Next, the sealing liquid 17 is slowly fed into the sample holder 11. In this manner, the surfaces of the liquid for analysis 16 except for the part that contacts with the sample holder 11 are surrounded by the sealing liquid 17, such that the liquid for analysis 16 is isolated from an external gas (shown in FIG. 3(*a*)). Then, a liquid drop of the liquid for analysis 16 is also adhered to a lower surface of the base 12 to surround the cantilever 14 and the probe 15, and then the base 12 is made to approach the sample holder 11 from an upper side thereof, such that the liquid drop on the lower surface of the base 12 is blended with the liquid drop of the liquid for analysis 16 in the sample holder 11 (shown in FIGS. 3(*b*) and 3(*c*)).

FIG. 4 is a schematic view of a main structure when an AFM is used to observe the sample 13 in the solution cell. The AFM includes: a three-dimensional (3-D) scanner 21, for making the sample 13 to move along the directions of X-Y-Z axis, and a displacement detecting system, for detecting a displacement of the cantilever 14 along the direction of the Z axis. The 3-D scanner 21 carries the sample holder 11, and the base 12 with the cantilever 14 fixed thereon is installed at a position, corresponding to the 3-D scanner 21, on the main body of the AFM. The scanner 21 is approximately barrel-shaped, which includes piezoelectric elements, and respectively moves freely within a set range along the direction of the X axis, the Y axis, and the Z axis under an external applied voltage. The displacement detecting system includes a laser source 22 for irradiating the laser beam to a place near the front end of the cantilever 14, and an optical detector 23 for detecting the laser beam reflected by the cantilever 14, and the like. A bending angle of the cantilever 14 is detected by using an optical beam deflection principle, thereby the upper and lower motions of the cantilever 14 can be detected.

In the method for analyzing the sample in the liquid according to this embodiment, before the observation, a sealing structure described above is formed in the liquid cell through any of the above sequences, and the probe 15 is used to scan a surface of the sample 13 in the liquid used for the analysis 16, thereby observing the surface of the sample. When the front end of the probe 15 is made to approach the sample 13 (with a gap smaller than or equal to several nanometres), the atomic force (an attractive force or a repulsive force) may be generated between atoms of the front end of the probe 15 and that of the sample 13. Under such a state, the scanner 21 is made to scan the surface of the sample by means of moving the probe 15 with respect to the sample 13 in the X-Y plane. Meanwhile, a feed back control is performed on a distance (a height along the direction of the Z axis) between the probe 15 and the sample 13 in a manner of maintaining a constant atomic force. At this time, the feed back quantity along the direction of the Z axis corresponds to the roughness on the surface of the sample 13, so a 3D image of the surface of the sample may be obtained according to the feed back quantity.

In the above method for analyzing a sample according to this embodiment, when the liquid for analysis is sealed by the sealing liquid, the AFM is used to observe the surface of the sample, so as to reliably prevent the evaporation of the liquid for analysis; hence, the surface of the sample can be observed with a high accuracy. In addition, in the method for analyzing the sample according to this embodiment, the upper surface of the liquid for analysis contacts with the base, so the laser beam is not interfered by the sloshing of the liquid level when the surface of the sample is scanned, so as to obtain a stable image.

The method for analyzing the sample in the liquid of the present invention has been described above through the embodiment, but the present invention is not limited to the above embodiment, and the method may be appropriately modified within the scope of the present invention. For example, the above embodiment is demonstrated by using the AFM for observation, but the present invention may also be applied to various SPMs, such as an STM.

Figure 5A:
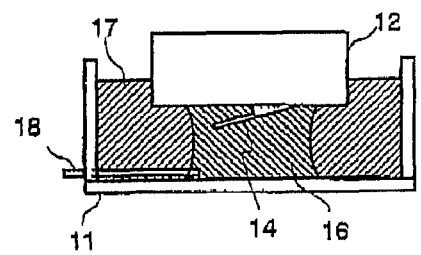
FIGS. 5(*a*) and 5(*b*) are cross-sectional views of a structure of a liquid cell when a cantilever sensor is used for an analysis, wherein FIG. 5(*a*) shows a liquid injection mechanism disposed on a sample holder, and FIG. 5(*b*) shows a liquid injection mechanism disposed on a base.
Figure 5B:
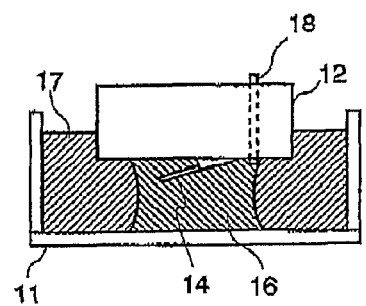
Figure 6A:
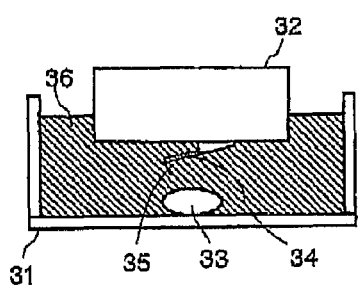
FIGS. 6(*a*) and 6(*b*) are cross-sectional views of a structure of a liquid cell according to a sample analyzing method in the conventional art, wherein FIG. 6(*a*) shows a state that the liquid is fully filled in the sample holder, and FIG. 6(*b*) shows a state that a liquid level is lowered due to evaporation of the liquid.
Figure 6B:
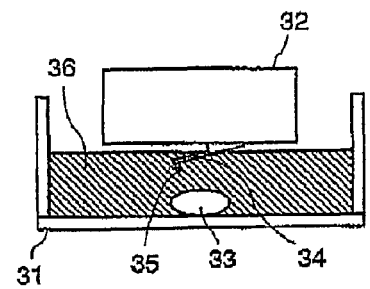
Figures 7A, 7B:
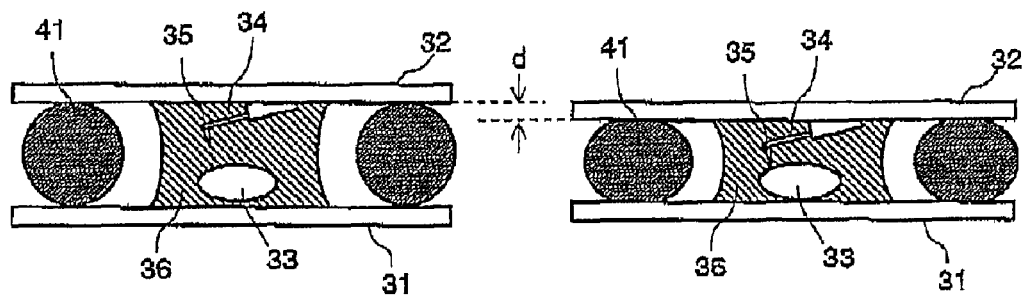
FIGS. 7(*a*) and 7(*b*) are schematic views of a method for preventing the evaporation of the liquid for analysis by using packing in the conventional art.

Furthermore, the method for analyzing a sample in a liquid of the present invention may not only be applied to analyze the surface properties of the sample by using various SPMs, the method may also be applied to detect minor constituents in the liquid by using a cantilever sensor. FIG. 5(*a*) shows an example of a structure of a liquid cell under such a situation. A substance capable of absorbing a substance to be detected (object substance) in a special manner is fixed on the surface of the cantilever 14, and the liquid for analysis 16, in which the cantilever 14 is immersed therein, is sealed by using the sealing liquid 17. Such a sealing state is formed in a same manner as any of the above sequences. However, when the sealing state is formed, the sample is not disposed in the liquid for analysis 16; after the sealing state is formed, the sample is fed into the liquid for analysis 16 by using a liquid injection mechanism 18 disposed on the sample holder 11. The liquid injection mechanism 18 has a pipe shape, which is configured from an outer part of the sample holder 11 to pass through the peripheral surfaces of the sample holder 11 to reach the neighbourhood of the inner centre of the sample holder 11. The flow path in the inner part may be opened or closed by using a switching device (not shown). Furthermore, the structure of the liquid injection mechanism 18 is not limited to the above structure. For example, as shown in FIG. 5(*b*), the liquid injection mechanism 18 may also be disposed on the base 12 that is used for fixing the cantilever. In this case, the liquid injection mechanism 18 is disposed at such a position that the optical path of the laser beam is not interfered.

When the solution cell is used and the cantilever sensor is adopted for an analysis, a resonance frequency of the cantilever 14 is first measured by using a specified method when the sample liquid has not been guided into the liquid for the analysis 16. Then, the sample liquid is fed into the liquid for analysis 16 by using the liquid injection mechanism 18, and similarly, the resonance frequency of the cantilever 14 is measured. If the sample liquid includes an object substance, the object substance is absorbed, such that the mass of the cantilever 14 increases. As the mass increases, the resonance frequency of the cantilever 14 changes correspondingly. Therefore, the object substance in the sample liquid may be detected by detecting the changes of the resonance frequency of the cantilever 14 before and after the sample liquid is fed into the liquid for analysis.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A method for analyzing a sample in a liquid, wherein a scanning probe microscope (SPM) is used for enabling a probe disposed on a front end of a cantilever to approach a surface of the sample immersed in the liquid, then the surface of the sample is scanned, and an interaction between the sample and the probe is detected, thereby generating an image, the method comprising:

filling a sealing liquid, which is immiscible with a liquid used for an analysis, around the liquid used for the analysis, wherein the sample and the probe are immersed therein, so as to form a sealing state for isolating the liquid used for the analysis from an external gas, wherein the sealing state is formed through the following steps:

adhering a liquid drop of the liquid used for the analysis to an inner part of a sample holder, which has an opened upper surface and is capable of being fully filled up with a liquid;

adhering the liquid drop of the liquid used for the analysis to a lower surface of a base having the fixed cantilever in a manner of surrounding the cantilever;

making the base to approach the sample holder, so as to blend the liquid drops of the liquid used for the analysis adhered respectively to the base and the sample holder; and feeding the sealing liquid into the sample holder for the sealing liquid to surround the liquid used for the analysis.

2. A method for analyzing a sample in a liquid, wherein a cantilever sensor is used for enabling a cantilever, in which a substance capable of absorbing an object substance is fixed on a surface of the cantilever, to immerse in the liquid, and detects the object substance by detecting an interaction between the object substance dissolved or dispersed in the liquid and a surface of the cantilever, the method comprising:

filling a sealing liquid, which is immiscible with a liquid used for an analysis, around the liquid used for the analysis with the cantilever immersed therein, so as to form a sealing state, wherein the liquid used for the analysis is isolated from an external gas, wherein the sealing state is formed through the following steps:

adhering a liquid drop of the liquid used for the analysis to an inner part of a sample holder, which has an opened upper surface and is capable of being fully filled up with a liquid;

filling the sealing liquid into the sample holder for the sealing liquid to surround the liquid drops of the liquid used for the analysis;

adhering the liquid drop of the liquid for the analysis to a lower surface of a base having the fixed cantilever in a manner of surrounding the cantilever;

making the base to approach the sample holder, so as to blend the liquid drops of the liquid used for the analysis adhered respectively to the base and the sample holder.

3. A method for analyzing a sample in a liquid, wherein a scanning probe microscope (SPM) is used for enabling a probe disposed on a front end of a cantilever to approach a surface of the sample immersed in the liquid, then the surface of the sample is scanned, and an interaction between the sample and the probe is detected, thereby generating an image, the method comprising:

filling a sealing liquid, which is immiscible with a liquid used for an analysis, around the liquid used for the analysis, wherein the sample and the probe are immersed therein, so as to form a sealing state for isolating the liquid used for the analysis from an external gas, wherein the sealing state is formed through the following steps:

adhering a liquid drop of the liquid used for the analysis to an inner part of a sample holder, which has an opened upper surface and is capable of being fully filled up with a liquid;

filling the sealing liquid into the sample holder for the sealing liquid to surround the liquid drops of the liquid used for the analysis;

adhering the liquid drop of the liquid for the analysis to a lower surface of a base having the fixed cantilever in a manner of surrounding the cantilever;

making the base to approach the sample holder, so as to blend the liquid drops of the liquid used for the analysis adhered respectively to the base and the sample holder.

4. A method for analyzing a sample in a liquid, wherein a cantilever sensor is used for enabling a cantilever, in which a substance capable of absorbing an object substance is fixed on a surface of the cantilever, to immerse in the liquid, and detects the object substance by detecting an interaction between the object substance dissolved or dispersed in the liquid and a surface of the cantilever, the method comprising:

filling a sealing liquid, which is immiscible with a liquid used for an analysis, around the liquid used for the analysis, wherein the sample and the probe are immersed therein, so as to form a sealing state for isolating the liquid used for the analysis from an external gas, wherein the sealing state is formed through the following steps:

adhering a liquid drop of the liquid used for the analysis to an inner part of a sample holder, which has an opened upper surface and is capable of being fully filled up with a liquid;

filling the sealing liquid into the sample holder for the sealing liquid to surround the liquid drops of the liquid used for the analysis;

adhering the liquid drop of the liquid for the analysis to a lower surface of a base having the fixed cantilever in a manner of surrounding the cantilever;

making the base to approach the sample holder, so as to blend the liquid drops of the liquid used for the analysis adhered respectively to the base and the sample holder.

5. The method for analyzing a sample in a liquid according to claim 1, wherein:

in the step of adhering the liquid drop of the liquid used for the analysis to the inner part of the sample holder, the sample is disposed in the liquid drop.

6. The method for analyzing a sample in a liquid according to claim 5, wherein:

the sealing liquid is a Fluor-inert liquid.

7. A base or a sample holder, suitable for being used in the method for analyzing a sample in a liquid according to claim 1, wherein the base or the sample holder comprises a liquid injection mechanism, for injecting a liquid to the liquid used for the analysis after a sealing state is formed.

8. The method for analyzing a sample in a liquid according to claim 2, wherein:

in the step of adhering the liquid drop of the liquid used for the analysis to the inner part of the sample holder, the sample is disposed in the liquid drop.

9. The method for analyzing a sample in a liquid according to claim 3, wherein:

in the step of adhering the liquid drop of the liquid used for the analysis to the inner part of the sample holder, the sample is disposed in the liquid drop.

10. The method for analyzing a sample in a liquid according to claim 4, wherein:

in the step of adhering the liquid drop of the liquid used for the analysis to the inner part of the sample holder, the sample is disposed in the liquid drop.

11. The method for analyzing a sample in a liquid according to claim 1, wherein:

the sealing liquid is a Fluor-inert liquid.

12. The method for analyzing a sample in a liquid according to claim 2, wherein:

the sealing liquid is a Fluor-inert liquid.

13. The method for analyzing a sample in a liquid according to claim 3, wherein:

the sealing liquid is a Fluor-inert liquid.

14. The method for analyzing a sample in a liquid according to claim 4, wherein:

the sealing liquid is a Fluor-inert liquid.

15. A base or a sample holder, suitable for being used in the method for analyzing a sample in a liquid according to claim 2, wherein the base or the sample holder comprises a liquid injection mechanism, for injecting a liquid to the liquid used for the analysis after a sealing state is formed.

16. A base or a sample holder, suitable for being used in the method for analyzing a sample in a liquid according to claim 3, wherein the base or the sample holder comprises a liquid injection mechanism, for injecting a liquid to the liquid used for the analysis after a sealing state is formed.

17. A base or a sample holder, suitable for being used in the method for analyzing a sample in a liquid according to claim 4, wherein the base or the sample holder comprises a liquid injection mechanism, for injecting a liquid to the liquid used for the analysis after a sealing state is formed.

\* \* \* \* \*